United States Patent [19]

Creighton

[11] Patent Number: 5,438,057
[45] Date of Patent: Aug. 1, 1995

[54] PHARMACEUTICAL COMPOSITIONS

[75] Inventor: Andrew M. Creighton, Mill Hill, England

[73] Assignee: British Technology Group Limited, London, England

[21] Appl. No.: 39,464

[22] Filed: Apr. 23, 1993

[30] Foreign Application Priority Data

Jul. 12, 1991 [GB] United Kingdom ............... 9115596

[51] Int. Cl.$^6$ ............................................ A61K 31/495
[52] U.S. Cl. .................................... 514/252; 544/357
[58] Field of Search ........................ 514/252; 544/357

[56] References Cited

U.S. PATENT DOCUMENTS

| 3,164,580 | 1/1965 | Matson | 260/132 |
| 3,196,153 | 7/1965 | Dazzi | 260/268 |
| 3,941,790 | 3/1976 | Creighton | 260/268 DK |
| 4,051,137 | 9/1977 | Ramey et al. | 260/268 TR |
| 4,275,063 | 6/1981 | Creighton | 424/250 |
| 4,404,381 | 9/1983 | Woo | 544/357 |
| 4,432,907 | 2/1984 | Wieder et al. | 260/429.2 |
| 4,755,619 | 7/1988 | Creighton et al. | 560/169 |
| 4,902,714 | 2/1990 | Creighton et al. | 514/459 |
| 5,149,710 | 9/1992 | Creighton et al. | 514/547 |
| 5,162,372 | 11/1992 | Creighton et al. | 514/547 |
| 5,278,187 | 1/1994 | Creighton et al. | 514/459 |

FOREIGN PATENT DOCUMENTS

| 0409499A2 | 1/1991 | European Pat. Off. . |
| 2278324 | 2/1976 | France . |
| 1967027 | 9/1976 | Germany . |
| 2511891 | 10/1976 | Germany . |
| 2511892 | 10/1976 | Germany . |
| 1941564 | 1/1979 | Germany . |
| 49-75524 | 7/1974 | Japan . |
| 61-152660 | 12/1984 | Japan . |
| 723316 | 2/1955 | United Kingdom . |
| 978724 | 12/1964 | United Kingdom . |
| 1001157 | 8/1965 | United Kingdom . |
| 7100/71 | 3/1971 | United Kingdom . |
| 1374979 | 11/1974 | United Kingdom . |
| 0330381 | 8/1989 | United Kingdom . |
| WO91/00729 | 1/1991 | |

WO92/00740 1/1992 WIPO .

OTHER PUBLICATIONS

E. H. Herman et al. "Comparison of the Protective . . ." Res Comm in Chem Pathology & Pharmaco.ilogy, vol. 48 No. 1, Apr. 1985, pp. 39–55.
V. J. Ferrans et al. "Pretreatment with ICRF–187 . . . " Dev Oncolog 1988, vol. 53, pp. 56–63.
A. N. El–Hage et al. "Examination of the Protective . . . " Toxicology, 18 (1988) pp. 295–303.
A. N. El–Hage et al. "Reduction in the Diabetogenic . . . " Res Comm in Chem Pathology & Pharmacology, vol. 33, No. 3, Sep. 1981, pp. 509–523.
M. J. Willes et al. "Lead poisoning—a potentially . . . " Pizen. Lek. Sborn. Suppl. 1985, pp. 113–115.
Z. Huang et al. "Metal binding by pharmaceuticals . . . " Agents and Actions 1984, pp. 536–542.
P. M. May et al. "Metal binding by pharmaceuticals . . . " Agents and Actions, vol. 15, ¾ (1984), pp. 448–453.
U. Witting et al. "Lead Elimination by ICRF 158 . . . " Int. Arch. Env. Occup. Health (1981), pp. 89–98.

(List continued on next page.)

Primary Examiner—James H. Reamer
Attorney, Agent, or Firm—Nixon & Vanderhye

[57] ABSTRACT

A compound of formula (II):

$$R_3N\begin{matrix}CO-CH_2\\ \\CO-CH_2\end{matrix}N-CHR_1-CHR_2-N\begin{matrix}CH_2-CO\\ \\CH_2-CO\end{matrix}NR_3$$

in which $R_1$ and $R_2$ together form a methylene or ethylene bridging group and $R_3$ is a hydrogen, an acyclic aliphatic hydrocarbon group having a maximum of six carbon atoms or a group $CH_2R_4$ in which $R_4$ is a $C_{1-5}$ alkyl group substituted by a hydroxy group or by a $C_{1-6}$ alkoxy group, or a salt thereof formed with a physiologically acceptable inorganic or organic acid, are of value for use in therapy, particularly as cardioprotective agents.

7 Claims, No Drawings

OTHER PUBLICATIONS

Z. Huang et al. "Metal binding properties of two homologues . . . " Inorganica Chimica Acta 1985, pp. L29–L32.

E. H. Herman et al. "Comparison of the effectiveness of (±) . . . " Cancer Research, 45, Jan. 1985, pp. 276–281.

E. H. Herman et al. "Reduction of chronic doxorubicin cardiotoxicity . . . " Cancer Research 41, Sep. 1981, pp. 3436–3440.

D. D. Von Hoff et al. "Phase 1 study of ICRF–187 using . . . " Cancer Treatment Reports, vol. 65 No. 3–4, Mar./Apr. 1981, pp. 249–252.

E. H. Herman et al. "Reduction of chronic daunorubicin . . . " Res. Comm. in Chem Pathology & Pharmacology, vol. 31, No. 1, Jan. 1981, pp. 85–97.

E. H. Herman et al. "Influence of Vitamin E and ICRF–187 . . . "Laboratory Investigation, vol. 49 No. 1 (1983), pp. 69–77.

E. Herman et al. "Reduction of Daunorubicin lethality . . . " Cancer Treatment Reports, vol. 63 No. 1 (Jan. 1979), pp. 89–92.

Brian B. Hasinoff. "The interaction of the cardioprotective . . . " Agents and Actions, vol. 26 No. ¾ (1989), pp. 378–385.

A. M. Creighton et al. "Antitumor activity in a series of . . . " Nature, vol. 222, Apr. 26, 1969, pp. 384–385.

A. M. Creighton. "Bisdiketopiperazines: A new class of antitumor . . . " Prog. in Antimicrobial & Anticancer chemotherapy, 1970, pp. 167–169.

J. C. Cai et al. "MST–16 and ZSB14 21, new antitumor agents" Poster, 14th Intl Congress of Chem. Jun. 23–28, 1985, pp. 1–9.

A. M. Creighton et al. "Ester Amide derivatives of ethylenediamine . . . " Recent Advances in Chemotherapy, Proc. of 14thInlt Cong of Chem. 1985, pp. 481–482.

U. Witting et al. "Der Enflu . . . " International Arch. Occup. Env. Health, 1979, pp. 365–373.

Z. Tanmu et al. "Pharmacological studies on bimolane . . . " Acta Pharmaceutica Sinica, vol. XV No. 10 (Oct. 1980), pp. 582.

S. A. Mortensen et al. "Clinical & non–invasive assessment of . . . " Int. J. Clin Pharm Res VI (2) (1986), pp. 137–150.

J. L. Speyer et al. "Protective effect of the . . . "New England Journal of Medicine, vol. 319 No. 12, pp. 745–752 (1988).

Chemical Abstarct #124811c "Acid Amides" vol. 82 (1975) p. 513. R. P. Houghton Synthesis of Bis . . . J Chem Soc Perkin Trans I 1982, p. 2693.

E. H. Herman et al. "Pretreatment with ICRF–187 . . . " Cancer Chemother Pharmacol (1986) 16:, pp. 102–106.

E. H. Herman et al. "Reduction of chronic . . . "Cancer Chemother. Pharmacol. 1986, pp. 277–281.

A. M. Creighton et al. "The effect of bisdioxopiperazines . . . " Proceedings of the Biochemical Society, p. 58 (1992).

D. T. Witiak et al. "Syntheses and $^1$H NMR Conformational . . . "J. Org. Chem. 1991, 56, pp. 5408–5417.

D. T. Witiak et al. "Stereoselective effects of cis- and trans-. . . "Jour of Medicinal Chem vol. 21 No. 12 (1978), pp. 1195–1197.

D. T. Witiak et al. "Study of trans-cyclopropybis . . . " Journal of Medicinal Chemistry, 1977, vol. 20 No. 5, pp. 630–635.

U. Witting et al. "Lead elimation by ICRF–158 in rats . . . " Int Arch Occup Environ Health 1979, 87–90.

Chemical Abstracts #197550d, vol. 93 No. 21 Nov. 24 (Columbus, Ohio, USA).

Chemical Abstracts #136564m, vol. 88 No. 19 May 8, 1978 (Columbus, Ohio, USA).

Zwilling, B. S. et al "Effect of stereoisomer . . . "Brit. J. Cancer, vol. 44, No. 4 (1981), pp. 578–583.

Herman, E. H. et al "Biological properties of ICRF–159 . . . "Advances in Pharmacology & Chemo., vol 19. (1982), pp. 254–257, 278–286.

Woodman, R. J. et al "Enhancement of the effectiveness . . . "Cancer Chemotherapy Reports, vol. 59 No. 4 part 1 Jul./Aug. 1975, pp. 689–695.

Hempeol, A. et al "Stereochemistry of conformationally . . . " Journal of the Chemical Society, vol. 104 No. 12 (1982), pp. 3456–3458.

E. H. Herman et al "Comparison of the protective . . . " Research Comm. in Chemical Pathology & Pharmacology, vol. 48 No. 1 (Apr. 1985), pp. 39–55.

T. K. Yeung et al. "ICRF 197: a new agent for protecting against . . . " Cellualr Pharmacology Laboratory, ICRF, London WC2A 3PX & CRC Normal Tissue Radiobiology Research Group, Oxford, OX3 7LJ, pp. 3–8.

PHARMACEUTICAL COMPOSITIONS

This application is a 371 of EB92/01256, filed Jul. 10, 1992.

This invention relates to pharmaceutical compounds and to compositions containing them, being primarily concerned with substances of use as cardioprotective agents and in certain other protective roles.

BACKGROUND OF THE INVENTION

Certain bis-dioxopiperazines of formula (I) are cytotoxic and have been used in the treatment of cancer. Thus UK patent 1,234,935 describes the compounds of formula (I) having $R=CH_3$ and $R'=R''=H$ (as the dl, d and l isomers); $R=R'=R''=H$; $R=R'=CH_3$ and $R''=H$ (as the meso isomer); and $R+R'=-CH_2CH_2-$ and $R''=H$. Of these the first named compound has proved to be of most value although a further compound of formula (I) having $R=R'=H$ and

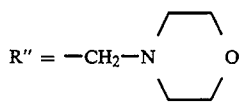

has also been used in treating cancer.

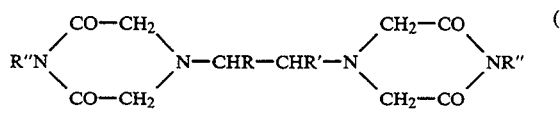

In UK Patent 2,173,195 pro-drugs of bis-dioxopiperazines of formula (I) such as those of UK Patent 1,234,935 are described. In the case of these pro-drugs the activity is indicated as extending to cardioprotection in addition to the treatment of cancer.

Studies have been reported by various authors on the chelating properties of these bis-dioxopiperazines and the use in treatment of lead poisoning has been proposed by Wittig and Hultsch, Int. Arch. Occup. Environ. Health, 1981, 48, 89, for the compound of formula (I) having $R=R'=H$ and $R''=CH_3$ and by May et al, Agents and Actions, 1984, 15, 448 and Willes and Williams, Plzen. Lek. Sborn., 1985, 49, 113, for the compound having $R=R''=H$ and $R'=C_2H_5$ in the dl form.

German Offenlegungsschrift 2,511,891 describes the use of certain bis-dioxopiperazines of formula (I) for the treatment and prophylaxis of thrombosis and embolism. These compounds (I) include, inter alia, those in which R and R' are linked so as to form a cycloalkyl residue of unspecified size and R'' is $C_{1-6}$ alkyl, with the sum of the carbon atoms in R, R' and R'' being greater than two.

In Research Communications in Chemical Pathology and Pharmacology, 1985, 48, 39, Herman et al report tests on the protective effect against acute daunorubicin toxicity of a range of bis-dioxopiperazines of formula (I). They conclude that although the compound bimolane

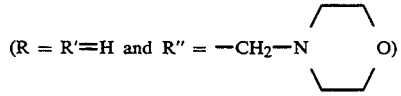

and the compound having $R=CH_3$ and $R'=R''=H$ (as the dl, d or l isomer) give protection against the lethal effects of daunorubicin, the remainder of the compounds tested ($R=R'=R''=H$; $R=R'=H$ and $R''=CH_3$; $R=R''=CH_3$ and $R'=H$ (l); $R=R'=CH_3$ and $R''=H$ (meso); $R=C_2H_5$ and $R'=R''=H$ (dl); R: $CH_3$, $R'=C_2H_5$ and $R''=H$ (dl-erythro); and $R+R'=-CH_2-CH_2-$ and $R''=H$; as well as the compound in which $-CHR-CHR'-$ is replaced by $-(CH_2)_3-$ and the ring opened bis-diacid diamide compound having $R=CH_3$ and $R'=H$) all showed either no protective activity or only minimal protective activity.

Despite the indications to the contrary in this Herman et al paper to the effect that of the bis-dioxopiperazine drugs only bimolane and the compound having $R=CH_3$ and $R'=R''=H$ are of value as cardioprotective agents, we have now found that certain other bis-dioxopiperazine drugs may with advantage be used as protective agents, in particular as cardioprotective agents. These bis-dioxopiperazines are of especial interest for providing protection against the cardiotoxic effects of various anthracycline drugs and in particular of doxorubicin (adriamycin). In this context it is relevant that, in addition to the comments in the Herman et al Research Communications in Chemical Pathology and Pharmacology paper, it is indicated by Herman et al in Advances in Pharmacology and Chemotherapy, 1982, 19, 249 that even the cardioprotective compound ICRF 159, which is the dl isomer of the compound of formula (I) having $R=CH_3$ and $R=R'=H$, is consistently more effective in reducing high dose daunorubicin toxicity than doxorubicin toxicity.

DESCRIPTION OF THE INVENTION

Accordingly the present invention comprises the use of a compound of formula (II):

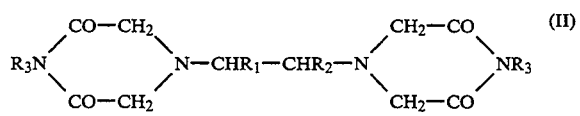

in which $R_1$ and $R_2$ together form a methylene or ethylene bridging group and $R_3$ is hydrogen, an acyclic aliphatic hydrocarbon group having a maximum of six carbon atoms or a group $CH_2R_4$ in which $R_4$ is a $C_{1-5}$ alkyl group substituted by a hydroxy group or by a $C_{1-6}$ alkoxy group, or a salt thereof formed with a physiologically acceptable inorganic or organic acid, for the manufacture of a medicament for use as a cardioprotective agent.

As indicated, $R_1$ and $R_2$ together form a methylene or ethylene bridging group, the preference being for a group $R_1+R_2$ which is $-CH_2-CH_2-$. Such a bridging group may have either the cis or especially the trans configuration, a trans-ethylene bridging group being particularly preferred.

As regards the group $R_3$ this is conveniently selected from unsubstituted aliphatic hydrocarbon groups or especially hydrogen. The term acyclic aliphatic hydrocarbon group is used herein to include both branched and especially straight chain groups. The group may be unsaturated or especially saturated, conveniently containing one double or triple bond in the former case. Thus, in particular, the groups may be alkenyl, alkynyl and particularly alkyl groups, which may be straight or branched chain. The aliphatic hydrocarbon groups conveniently contain a maximum of four or especially three carbon atoms, preferred groups therefore being $C_1$–$C_4$ or $C_1$–$C_3$ alkyl groups and $C_2$–$C_4$ or $C_2$–$C_3$ alkenyl and alkynyl groups. When $R_3$ is not hydrogen it is preferably an alkyl group, for example ethyl or particularly methyl where $R_3$ is an unsaturated aliphatic hydrocarbon group, however, it preferably has the form $CH_2R_5$ where $R_5$ is a $C_{2-5}$ alkenyl or alkynyl group, preferably a $C_2$ or $C_3$ group, for example $CH_2R_8$ being allyl or propargyl.

As regards the groups $R_3$ of the form $CH_2R_4$, these may be branched or especially straight chain alkyl groups substituted, particularly terminally, by a hydroxy group or particularly by an alkoxy group. Conveniently the groups $R_4$ are substituted alkyl groups of 1 to 2 or 1 to 3 carbon atoms, substituted ethyl and particularly substituted methyl groups being of most interest. Preferred alkoxy group substituents similarly contain 1 to 3 or 1 to 4 carbon atoms with ethoxy and particularly methoxy groups being of most interest. Conveniently the total number of carbon atoms in such an alkoxyalkyl group $CH_2R_4$ is from 3 to 6, especially 3 or 4.

Compounds of particular interest are those in which $R_3$ is selected from 2-hydroxyethyl, 2-methoxyethyl, more particularly ethyl, n-propyl and isopropyl, and most particularly methyl and especially hydrogen, for example together with values of $R_1$ and $R_2$ indicated as preferred.

Specific preferred compounds according to the present invention are thus those in which $R_1$ and $R_2$ are an ethylene bridging group, together with a group $R_3$ which is ethyl, particularly methyl or especially hydrogen. Among these compounds may particularly be mentioned the compound 1,2-bis(3,5-dioxopiperazin-1-yl)cyclobutane, especially the trans isomer thereof.

The compounds may exist in various stereochemical forms, each of which is included by the present invention. Thus, the existence of cis and trans isomers for each of the compounds of the invention has already been discussed. Moreover the trans compounds can exist in enantiomorphic d and l forms. In some cases the optically active d- and l forms may have the advantage of significantly higher water solubility than the corresponding racemate and it may also be the case that the biological activity of the compound will differ as between the isomers. The invention therefore extends to the use of the trans compounds not only as the dl-racemate but also in a form in which the amount of the compound in either the d or l form is greater than that in the l or d form, respectively (including amounts in that configuration present in the dl racemate). In particular the compound may be essentially in the form of the d or l isomer, for example being substantially free from (i.e. the compound contains no more than 20% and more conveniently no more than 10% of) the dl and l or dl and d isomers. However, particularly where the advantage lies in enhanced solubility of the optically active isomers compared with the racemate, rather than enhanced biological activity for one isomer, any enhancement of the proportion of one isomer should have some significant effect.

The preferred compound trans-1,2-bis(3,5-dioxopiperazin-1-yl)cyclobutane may thus be used in the dl-, d- or l- form.

It will be appreciated that certain of the compounds of formula (II) as defined hereinbefore have not previously been specifically described in the literature and that the present invention therefore extends to such compounds per se and to these compounds for use in therapy. Such compounds include those in which $R_3$ is other than hydrogen and also the cis and trans compounds in which $R_3$ is hydrogen when $R_1$ and $R_2$ together form an ethylene bridging group but in the case of the trans compound only when it is in the form of the d or l enantiomer rather than the dl racemate.

Several methods are available for the preparation of the compounds of formula (II). Thus, for example, compounds wherein $R_3$ is hydrogen can be prepared by reaction of the corresponding tetra-acetic acid of formula (III) with formamide, this reaction usually being carried out in an excess of formamide as the solvent and at an elevated temperature, preferably under nitrogen.

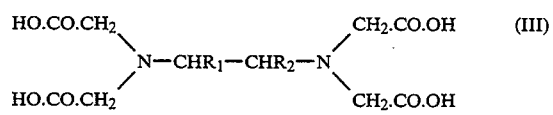

Alternatively, and with particular advantage when the tetra-acetic acid (III) has a tendency to decarboxylate on heating, the compounds (II) having $R_3$=H can be prepared by heating the corresponding tetra-amide in polyphosphoric acid or phenol.

A further alternative for the preparation of compounds having $R_3$=H also exists, having the advantage of being a lower temperature method, which comprises treating the corresponding tetranitrile with sodamide in formamide and treating the resulting product with hydrogen chloride in methanol.

The compounds of formula (II) wherein $R_3$ is other than hydrogen may conveniently be prepared by reaction of the corresponding tetra-acetic acid of formula (III) as described above but with an N-substituted formamide in which the nitrogen atom is substituted by a group $R_3$ instead of with formamide.

The tetra-acetic acids of formula (III) may conveniently be obtained from the corresponding dicarboxy acid of formula (IV) and the tetra-amides from the corresponding tetra-acetic acid.

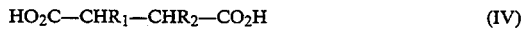

Examples of such procedures and/or of intermediates of use in such procedures are to be found in UK patents 723,316, 966,802, 978,724, 1,234,935 and 1,374,979, and in German Offenlegungsschrift 2,511,891.

In general terms, a process for the preparation of a compound of formula (II) as defined hereinbefore and salts thereof formed with a physiologically acceptable inorganic or organic acid from a compound of the formula (V)

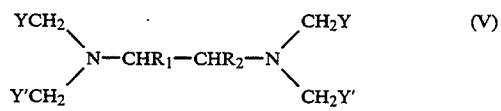

in which $R_1$ and $R_2$ are as defined for the compound of formula (II), comprises:
(a) heating an N,N,N',N'-tetracarboxymethyl diamine of formula (V) in which Y and Y' represent carboxy groups, or the bis anhydride thereof wherein Y and Y' together represent a —CO.O.CO— group, with an acid amide of the formula RCONHR₃ in which R represents hydrogen, an aliphatic residue, for example a $C_{1-4}$ alkyl group or an amino group $NH_2$, and $R_3$ is as defined for the compound of formula (II);

(b) reacting, either by heating or by treatment with a base, an N,N,N',N'-tetracarboxymethyl diamine of formula (V) in which Y and Y' represent carboxy groups, the bis anhydride thereof in which Y and Y' together represent a —CO.O.CO— group, a tetra-halide thereof in which Y and Y' each represent a group COX in which X is a halogeno group, for example chloro or bromo, or a tetra-ester thereof in which Y and Y' each represent a group $CO_2X'$ in which X' is an aliphatic or aromatic residue, for example a $C_{1-4}$ alkyl group or a substituted or unsubstituted phenyl group, with a stoichiometric amount of ammonia when $R_3$ is hydrogen in the compound of formula (II) or otherwise of an amine of the formula $H_2NR_3$ in which $R_3$ is as defined for the compound of formula (II);

(c) treating a di-ester of a N,N'-dicarboxymethyl-N,N'-dicarbamoylmethyl diamine (or when $R_3$ is other than hydrogen a corresponding compound which contains substituted carbamoyl groups) of formula (V) in which Y represents a group $CO_2X'$ in which X' is as defined under (b) and Y' represents a group CONHR₃ in which $R_3$ is as defined for the compound of formula (II), with a base, for example an alkali metal hydroxide such as sodium hydroxide in aqueous solution or an alkali metal alkoxide such as sodium methoxide in non-aqueous solution;

(d) heating an N,N'-dicarboxymethyl-N,N'-dicarbamoylmethyl diamine (or when $R_3$ is other than hydrogen a corresponding compound which contains substituted carbamoyl groups) of formula (V) in which Y represents a carboxy group and Y' represents a group CONHR₃ in which $R_3$ is as defined for the compound of formula (II), to effect cyclisation thereof;

(e) when $R_3$ is hydrogen in the compound of formula (II), heating an N,N,N',N'-tetracarbamoylmethyl diamine of formula (V) in which Y and Y' each represent a carbamoyl group, with an acidic reagent, for example polyphosphoric acid, phenol or boron trifluoride;

(f) when $R_3$ is hydrogen in the compound of formula (II), reacting an N,N,N',N'-tetracyanomethyl diamine of formula (V) in which Y and Y' represent cyano groups, with an alkali metal amide, for example sodamide, and treating the product with acid, for example with a mineral acid such as a hydrohalic acid;

(g) when $R_3$ is hydrogen in the compound of formula (II), reacting an N,N'-disubstituted 3,5,3',5'-tetraoxodipiperazine of formula (V) in which Y and Y' together represent a grouping —CO.NX".CO— wherein X" is a group convertible to hydrogen, to replace the group X" by hydrogen; and/or, where appropriate;

(h) separating the compound (II) with the required stereo-chemistry from other isomers thereof; and where appropriate converting the compound (II) to a physiologically acceptable addition salt thereof.

The preferred procedures are (a), (b), (d) and (e), and where appropriate (g) particularly as described hereinbefore. In the case of procedure (b), particularly when the reactant is ammonia rather than an amine, it is preferred to effect the reaction in an acid amide of the general formula

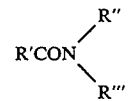

in which R' represents hydrogen or an aliphatic radical, for example an alkyl group, having one to four carbon atoms and R" and R''' represent the same or a different aliphatic radical, for example an alkyl group, having one to four carbon atoms or alternatively one of R" and R''' may with R' and the

group represent a five or six membered lactam ring.

In general the compounds (II) in which $R_1$ and $R_2$ together form a methylene bridging group are less stable than those in which $R_1$ and $R_2$ form an ethylene bridging group. Accordingly with such compounds it is preferred when using method (a) to use a less elevated temperature, for example about 95° C. instead of 150°–155° C., or to employ a method not requiring heating, for example method (b) with the use of a base, for example an alkali metal alkoxide such as sodium methoxide, to effect the reaction. Such milder reaction conditions may also be advantageous when preparing compound (II) in which $R_1$ and $R_2$ together form an ethylene group where these are of the cis configuration.

To obtain compounds (II) of the desired stereochemistry it is most convenient to use an intermediate compound having the equivalent stereochemistry, particularly as regards the preparation of geometrical isomers, but conveniently also as regards the preparation of optically active compounds. Thus the tetra-acetic acid, tetra-amide, tetra-nitrile, etc., which is used conveniently has the same stereochemistry as is desired in the final product. When a d or l isomer is required rather than the dl racemate. However, an alternative to the utilisation of a d or l intermediate compound, falling within method (b) described hereinfore is to effect a resolution of the racemic compound (II), for example using an appropriate optically active acid to form a mixture of salts of the d and l forms of the compound (II) which are then separated. Alternatively, it is possible to use a liquid chromatography system employing a chiral stationary phase to effect the separation.

The present invention also includes pharmaceutical compositions comprising as an active component such compounds of formula (II) as are described hereinbefore as being novel per se, together with a physiologically acceptable diluent or carrier. In general, compositions containing the compounds of formula (II) which are of particular interest are those in which the diluent or carrier excludes any liquid which is not sterile and pyrogen free.

As indicated, the compounds (II) may be formulated as salts formed with physiologically acceptable inorganic or organic acids. These salts may be prepared by conventional methods and it is preferred to use methane sulphonic acid, isethionic acid, lactic acid, tartaric acid or another solubilising acid.

The compounds of formula (II) may be formulated singly, or as a mixture of two or more compounds, for use as pharmaceuticals by a variety of methods. For instance, they may be applied as aqueous, oily (e.g. as a suspension inisopropyl myristate), or in some cases emulsified compositions for parenteral administration and therefore preferably sterile and pyrogen-free. Some of these compounds have rather low solubility in aqueous media and are therefore usually administered in the form of aqueous suspensions containing suitable surface active agents. It will be appreciated that the dosage levels used may vary over quite a wide range especially since certain of the compounds (II) are more active than others. However, without commitment to a rigid definition of dosages it may be stated that a daily dosage of active constituent (estimated as the free base), divided if necessary, of from 10 mg to 3 g is proposed for parenteral mammalian use. This dosage may conveniently be applied as a solution in 500–1000 ml of liquid for intravenous injection by slow infusion, or as a solution or suspension in about 10 ml of liquid by the intramuscular route, or in small volumes subcutaneously. (Parenteral, particularly intravenous, administration is the route preferred for use in conjunction with the anthracycline drugs so that injectable compositions are of especial interest.) More particularly, with many compounds (II) the daily dose for a 70 kg human, administered parenterally, will often be in the range from about 100 mg to about 500 mg but with the more active compounds it may be less than this (the dose being varied pro rata for humans of a different weight or other mammals). When used in conjunction with an anthracycline drug, where a single administration of the drug and the compound (II) is common, however, higher doses than this may often be employed, for example between about 500 mg and about 3 g, with doses of more than this being considered where appropriate in terms of the ratios of compound (II):anthracycline drug as discussed hereinafter.

Where appropriate, the substances may also be compounded for oral administration in dosages which may be similar but may often be somewhat higher, so that the daily dose for a 70 kg human may often be in a range from 100 mg to 1 g or even as high as 3 g for many compounds (II) but possibly somewhat less than this for the more active compounds. Such oral formulations may particularly take the form of tablets compounded in the presence of conventional solid carrier materials such as starch, lactose, dextrin and magnesium stearate, or of capsules or cachets. Suppositories, pessaries, aerosol and other formulations may also be employed. The compounds may be formulated in unit dosage form, i.e. in discrete portions each containing a unit dose, or a multiple or sub-multiple of a unit dose of the active ingredient.

The compounds (II) as defined hereinbefore are primarily of value as cardioprotective agents and it should be-noted that their potential in such a use extends not only to use in conjunction with drugs having a cardiotoxic side effect, these often being cytotoxic agents such as the anthracycline drugs, which are of particular value in treating breast cancer, but also extends to pathological conditions where the heart is at risk. The term "anthracycline drug" is used herein to include not only natural and semi-synthetic anthracyclines such as upirubicin, idarubicin, daunorubicin and especially doxorubicin (which names are used herein to include salts of these compounds), but also synthetic analogues of the anthracyclines such as mitoxantrone which also exhibit dose-limiting cardiotoxicity. Indeed, the compounds (II) are of value in providing cardioprotection against the cardiotoxic side effect of various compounds containing a moiety

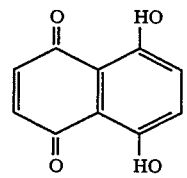

the toxic effect of such compounds being believed to derive from their ability to generate free radicals following chelating.

Another use of the compounds (II) as a protective agent is in protection against other toxic effects arising from natural diseases or induction by drugs, for example damage caused by free radicals. Free radicals have been implicated as damaging agents in the action of many toxins and in a number of diseases, for example reperfusion injury such as may occur following myocardial infarction, inflammatory conditions caused for example in rheumatoid arthritis. Drug induced damage can arise from various agents which are either toxic as such or when present in the body in excess, such agents including paracetamol (p-hydroxyacetanilide), and heavy metals, e.g. iron and aluminium.

The compounds (II) find most application in the treatment of humans although they can find veterinary use in certain other mammals such as dogs, rabbits, cattle, and horses.

When used as a cardioprotective agent in the context of a pathological condition where the heart is at risk as a result of that condition the compounds (II) are administered for a period dictated by the existence of this condition. When used in a cardioprotective role in conjunction with a drug having a cardiotoxic side effect, the period of administration will be related to that of the use of the drug which will usually be administered at normal dosage rates and by the usual regimen, often parenterally. The compounds (II) may conveniently be administered before, together with or less often after the drug, the choice depending to some extent on the particular drug in question. In the first and third usages both the compound (II) and the drug will each be formulated separately, usually in a conventional manner, for example both being formulated as described above, although the two compositions may be packaged together for ease of sequential administration to the patient. A suitable time lapse between administration of the compound (II) and the drug in either order is quite short, being no more than about 1 to 4 hours, for example 2 hours, and particularly being about 1 hour or somewhat less, depending on the drug in question.

When the compound (II) is administered together with the drug, the two may be formulated separately but it may be preferred to include the compound (II) and the drug in the same composition. Such a pharmaceutical composition may again conveniently take one of the forms described above for compositions containing only the compound (II) and may, if desired, contain more than one compound (II) and/or more than one drug. The present invention thus includes (a) a pharmaceutical composition which comprises a compound of formula (II), as defined hereinbefore, and a drug having a cardiotoxic or other toxic side effect, for example an anthracycline drug, together with a physiologically acceptable diluent or carrier, and also (b) a kit comprising in association a compound of formula (II), as defined hereinbefore, and a drug having cardiotoxic or other toxic side effect.

As indicated, the compounds (II) are of particular interest for use with doxorubicin and the present invention therefore particularly includes a pharmaceutical composition comprising a compound of formula (II) as defined hereinbefore and doxorubicin, together with a physiologically acceptable diluent or carrier.

In instances where a series of doses of the drug is administered it may not be necessary for each administration of the drug to be made concomitantly with, or at the interval given above after or before the administration of the compound (II). It may be possible to administer the compound (II) alone or together with the drug, followed by one or more repeated spaced doses of the drug alone or, more often, in view of the more rapid metabolisation of the compound (II), to administer the drug alone or together with the compound (II), followed by one or more repeated spaced doses of the compound (II) alone. If the treatment with the drug is continued over an extended period repeat doses of the compound (II) are also likely to be required and one possible regimen would involve the administration of the drug and compound (II) together on certain occasions followed by the compound (II) alone on others.

As regards the relative amounts of the compound (II) and a drug to be used, this will depend on both the particular compound (II), the drug used and the regimen of use, a good indication being provided, however, by the dosages indicated hereinbefore for the compounds (II) and the conventional doses used for the drug. However, some additional comments may be made concerning the proportions of compound or compounds (II) to anthracycline drug which are used either singly or together in a pharmaceutical composition containing both a compound or compounds (II) and an anthracycline drug. Thus, by way of guidance it may be stated that a dose ratio of between 5:1 to 20:1 or even 25:1 or 30:1 w/w of compound or compounds (II) to drug, especially about 10:1 w/w, is often suitable. By way of further guidance, it may be mentioned that a normal single dosage of doxorubicin is in the range of about 0.75 to 2 mg/kg, i.e. about 50 to 150 mg for a 70 kg human being, but that the use of the compounds (II) is intended to enable some increase in the dosage, for example to 4 or 5 mg/kg, if desired, in order to enhance the anti-cancer effect of the doxorubicin whilst its cardiotoxic side effects are controlled by the presence of the compound (II).

The exact dosage of an anthracycline drug such as doxorubicin which is used will depend on whether it is given with other anti-tumour agents. Thus anthracycline drugs are often given together with one or more of other such agents, for example fluorouracil and cyclophosphamide and where desired, a pharmaceutical composition containing a compound or compounds (II) and an anthracycline drug can contain other such antitumour agents. Moreover, it may be advantageous to administer a calcium supplement together with the compounds (II), this usually being administered separately.

When used as a protective agent against the toxic effect of paracetamol, the compounds (II) may be used protectively before occurrence of the toxicity or following occurrence of the toxicity. It may even be possible to formulate the compound (II) with paracetamol in order automatically to counter the effect of an overdose thereof. Broadly similar dosage levels may be used to those described hereinbefore although where the toxic effect is acute, as for example is usually the case following an overdose of paracetamol, higher dosages over a shorter period may be indicated.

Other forms of protection discussed hereinbefore include the use of the compounds (II) in conjunction with any condition which is either "naturally occurring" or drug induced where free radical damage occurs (this may also be involved in some of the conditions described hereinbefore such as a anthracycline drug-induced damage), for example in reducing the diabetogenic effect of drugs such as alloxan which generate free hydroxyl radicals. Reperfusion injury referred to hereinbefore is also believed to have a free radical cause. The compounds (II) may once again be used in a broadly similar manner as when employed in cardioprotection, including the dosage levels used.

The present invention thus includes a method for the treatment of a patient in need of cardioprotection or in need of protection against the toxic effects of paracetamol or against damage caused by free radicals which comprises administering to said patient a therapeutically effective amount of a compound of formula (II) as defined hereinbefore. As discussed hereinbefore, the administration is preferably effected in the form of a pharmaceutical composition containing the compound of formula (II) as an active ingredient thereof.

EXAMPLES

The present invention is illustrated by the following Examples.

Example 1: Preparation of (±) trans-1,2-bis(3,5-dioxopiperazin-1-yl)cyclobutane trans-1,2-Diaminocyclobutane tetra-acetic acid monohydrate (100 g) (melting point 234°-235° C.; prepared in 56% yield by the method of Dwyer and Garvan, J. Amer. Chem. Soc., 1959, 81, 2956), was heated with 400 ml of formamide under nitrogen at reduced pressure at 100°-110° C. for 1 hour and then at 150°-155° C. for 4 hours. The brown solution was evaporated under reduced pressure at 80°-90° C. and the residue taken up in 120 ml of methanol and cooled in a refrigerator overnight. Filtration, followed by washing with cold methanol and vacuum drying at 65° C. gave a 69% yield of (±) trans-1,2-bis(3,5-dioxopiperazin-1-yl)cyclobutane, melting point 257°-259° C. (decomposition)[1].

Example 2: Formulation of compounds (A) Tablets of the following composition are prepared:

|  | mg/tablet |
|---|---|
| Compound of Example 1 (micronised) | 250 |
| 'Avicel' (microcrystalline cellulose)* | 38 |
| polyvinylpyrrolidone | 3 |
| alginic acid | 6 |
| magnesium stearate | 3 |

*'Avicel' is a Registered Trade Mark or Service Mark.

(1) The preparation of cis-1,2-bis(3,5-dioxopiperazin-1-yl)cyclopropane by heating the tetramethyl ester of the corresponding tetra-acetic acid with sodium hydride and formamide in dimethoxy ethane at 95° C. is described by Witiak et al., J. Med. Chem., 1978, 21, 1194, whilst the preparation of the trans isomer of this compound by the reaction of the tetramethyl ester of the corresponding tetra-acetic acid with ammonia and sodium methoxide in methanol is described by Witiak et al., J. Med. them., 1977, 20, 630.

The compound of Example 1 is mixed with 'Avicel' and polyvinylpyrrolidone is added, dissolved in sufficient industrial methylated spirits (74° OP) to produce a mass suitable for granulating. The mass is granulated through a 20 mesh sieve and the resultant granules are dried at a temperature not exceeding 50° C. The dried granules are passed through a 20 mesh sieve and the alginic acid and magnesium stearate are then added and mixed with the granules. The product is compressed into tablets each weighing 300 mg on ⅜ inch flat bevelled edge divided punches.

(B) Tablets of the following composition are prepared:

|  | mg/tablet |
| --- | --- |
| Compound of Example 1 (micronised) | 250 |
| 'Avicel' (microcrystalline cellulose) | 134 |
| polyvinylpyrrolidone | 4 |
| alginic acid | 8 |
| magnesium stearate | 4 |

The tablets are prepared by essentially the same procedure as described in (A) and are compressed at a tablet weight of 400 mg on 7/16 inch flat bevelled edge punches.

(C) Tablets of the following composition are prepared:

|  | mg/tablet |
| --- | --- |
| Compound of Example 1 (micronised) | 250 |
| lactose (300 mesh) | 19 |
| maize starch | 15 |
| gelatine | 10 |
| magnesium stearate | 6 |

|  | mg/tablet |
| --- | --- |
| Compound of Example 1 (micronised) | 250 |
| 'Avicel' (microcrystalline cellulose)* | 38 |
| polyvinylpyrrolidone | 3 |
| alginic acid | 6 |
| magnesium stearate | 3 |

*'Avicel' is a Registered Trade Mark or Service Mark.

The tablets are prepared by mixing the compound of Example 1 with lactose and half the total quantity of maize starch required, and adding to the mass a 5% solution of gelatine in water. The product is granulated through a 16 mesh sieve, and the resultant granules are dried to constant weight at a temperature not exceeding 50° C. The dried granules are passed through a 20 mesh sieve and mixed with magnesium stearate and the remainder of the maize starch. The product is compressed at a 300 mg tablet weight on ⅜ inch flat bevelled edge divided punches.

Example 3: Cardioprotective effect of (±) trans-1,2-bis(3,5-dioxopiperazin-1-yl)cyclobutane against the toxicity of doxorubicin The experiments were conducted as follows.

Animals

Mature male Sprague Dawley rats, 13–14 weeks old, weighing 400–500 gm were used. The animals were caged in groups of three and were kept in a constant environment. They were fed 41-B cubed diet and water ad libitum. The animal house was maintained in an alternating 12-hour wake-sleep cycle.

Drug administration

The cardioprotective activity of (±) trans-1,2-bis(3,5-dioxopiperazin-1-yl)cyclobutane (hereinafter referred to as the compound) was studied in the rats. The compound was inadequately soluble in saline and was therefore administered as a uniform suspension in 0.5% sodium carboxymethyl cellulose (CMC) in normal saline. The suspension was prepared shortly before use and was administered at a constant injection volume of 1 ml per 100 gm body weight. Doxorubicin hydrochloride (hereafter referred to as doxorubicin) (Farmitalia, Milan, Italy) was dissolved in sterile water (2 mg/ml) before injection.

A group of 6 animals received a combined treatment of the compound and doxorubicin. The compound was administered to animals as a single intraperitoneal (i.p.) injection into the lower right quadrant of the abdomen to avoid damage to vital organs. An hour after the administration of the compound, the animals received a single intravenous (i.v.) injection of doxorubicin (4 mg/kg), via the femoral vein. A group of 10 animals received an i.p. injection of saline (1 ml/100 gm) followed by an i.v. injection of saline (0.2 ml/100 gm) one hour later. These rats acted as control animals. Nine animals received an i.p. injection of saline one hour before an i.v. administration of doxorubicin (4 mg/kg). To minimise the effects of circadian timing, doxorubicin administration was carried out between 13.30 hours and 15.30 hours. During intravenous drug administration and for subsequent cardiac output measurements, animals were anaesthetised with choral hydrate (300 mg/kg).

Assessment of toxicity

The animals were weighed daily for up to three weeks after receiving treatment. The maximum reduction in body weight over this period was used as an index for the assessment of general acute toxicity. Animals were also weighed at 4 and 8 weeks to assess the general toxicity of the drug.

The protective activity of the compound against doxorubicin-induced cardiotoxicity in the rats was assessed at 8 weeks by measuring the cardiac output in animals receiving the treatment using an external counting technique wherein a radioactive tracer, technetium ($^{99m}TcO_4$), was injected as a bolus into the femoral vein of an anaesthetised animal. The activity time curve over the heart was recorded at 0.1 second intervals for 40 seconds, using an NaI detector connected to a multichannel analyzer (ND-62, Nuclear Data). ECG and heart rate were determined concomitantly with the cardiac output measurement, using a human ECG monitor (Hewlett Packard 7830A) coupled to a scope memory (model VK-12-2, Seltek Instrument Ltd.) and a chart recorder.

Gross post mortem examinations were carried out on the animals that died during the study as well as those killed at the end of experiment (8 weeks).

In this study, statistical differences between group means were analysed using Student's t-test.

Results

The results are summarised in the Table.

All animals showed a transient reduction in body weight in the first three weeks after treatment. Animals receiving doxorubicin and pretreated with saline or the compound all showed a >10% reduction in body weight. Control animals, i.e. those receiving saline (i.p.) and saline (i.v.), showed a 3% reduction in body weight over this period; significantly less than animals receiving saline and doxorubicin (p<0.001).

Measurement in control animals at 8 weeks showed a mean cardiac output value of 222.4±5.8 ml/min/kg and a mean heart rate of 441±7 beats per minute. All control animals survived the course of study of 8 weeks, as did those receiving the compound and doxorubicin. Animals receiving saline and doxorubicin showed a 60% reduction in cardiac output and a 35% reduction in heart rate. In this group of animals, one animal died just before 8 weeks. Information concerning this animal was loss due to severe post mortem changes.

The compound showed significant activity against doxorubicin-induced cardiotoxicity. As will be seen from the Table, all of the animals receiving the compound (100, 150 or 200 mg/kg) survived the course of study of 8 weeks without showing any signs of congestive failure. Measurments in these animals showed significantly less impairment in cardiac output when compared to those receiving saline and doxorubicin (p<0.001). There was no change in heart rate measured in animals pretreated with the compound and the animals managed to maintain a normal growth with body weights not significantly different from those measured in control animals (p>0.5). There was no indication of dose dependent changes in the protective activity of the compound over the dose range studied.

$$R_3N\begin{matrix}CO-CH_2\\ \\ CO-CH_2\end{matrix}N-CHR_1-CHR_2-N\begin{matrix}CH_2-CO\\ \\ CH_2-CO\end{matrix}NR_3$$

in which $R_1$ and $R_2$ together form an ethylene bridging group and $R_3$ is hydrogen, an acyclic aliphatic hydrocarbon group having a maximum of six carbon atoms or a group $CH_2R_4$ in which $R_4$ is a $C_{1-5}$ alkyl group substituted by a hydroxy group or by a $C_{1-6}$ alkoxy group, or a salt thereof formed with a physiologically acceptable inorganic or organic acid.

2. The method according to claim 1, in which $R_3$ is a methyl group.

3. The method according to claim 1, in which $R_3$ is hydrogen.

4. The method according to claim 1, in which the ethylene bridging group has the trans configuration.

5. The method according to claim 1, in which the compound of formula (II) is dl-, d- or l-trans-1,2-bis(3,5-dioxopiperazin-1-yl)cyclobutane.

6. A method for the treatment of a patient in need of cardioprotection or in need of protection against the toxic effects of paracetamol or against damage caused by free radicals, which method comprises the step of administering to said patient a therapeutically effective amount of a compound of formula (II)

$$R_3N\begin{matrix}CO-CH_2\\ \\ CO-CH_2\end{matrix}N-CHR_1-CHR_2-N\begin{matrix}CH_2-CO\\ \\ CH_2-CO\end{matrix}NR_3$$

in which $R_1$ and $R_2$ together form a methylene or ethylene bridging group and $R_3$ is hydrogen, an acyclic aliphatic hydrocarbon group having a maximum of six carbon atoms or a group $CH_2R_4$ in which $R_4$ is a $C_{1-5}$ alkyl group substituted by a hydroxy group or by a $C_{1-6}$ alkoxy group, or a salt thereof formed with a physiologically acceptable inorganic or organic acid.

7. A method according to claim 1 in which the compound of formula II is cis-1,2-bis(3,5-dioxopiperazin-1-yl)cyclobutane.

TABLE

| Treatment | Dose (mg/kg) | No. of animals | W1 | W2 | W3 | ΔW(%) | RCO | RHR | Survival | Incidence of CHF |
|---|---|---|---|---|---|---|---|---|---|---|
| Control[1] | — | 10 | 410 ± 17 | 448 ± 16 | 495 ± 19 | 2.8 ± 0.6 | 1.00 ± 0.05 | 1.00 ± 0.02 | 10/10 | 0/10 |
| Saline[2] | — | 9 | 447 ± 11 | 381 ± 8 | 324 ± 27 | 11.6 ± 0.7 | 0.41 ± 0.04 | 0.65 ± 0.19 | 8/9[4] | 0/8 |
| Compound[3] | 100 | 6 | 465 ± 12 | 476 ± 18 | 497 ± 21 | 13.3 ± 0.3 | 0.80 ± 0.05 | 1.04 ± 0.03 | 6/6 | 0/6 |
|  | 150 | 6 | 444 ± 16 | 477 ± 16 | 486 ± 18 | 10.3 ± 1.2 | 0.86 ± 0.06 | 1.00 ± 0.04 | 6/6 | 0/6 |
|  | 200 | 6 | 465 ± 12 | 482 ± 16 | 500 ± 26 | 13.9 ± 1.1 | 0.84 ± 0.05 | 1.05 ± 0.03 | 6/6 | 0/6 |

Key
[1]animals receiving: saline (i.p.) + saline (i.v.) after 1 hour
[2]animals receiving: saline (i.p.) + doxorubicin (4 mg/kg, i.v.) after 1 hour
[3]animals receiving: the compound (i.p.) + doxorubicin (4 mg/kg, i.v.) after 1 hour
[4]animal died just before 8 weeks. Information on this animal lost due to severe post mortem changes.
W1, W2 and W3: mean body weight of animals at the time of injection and at 4 weeks and 8 weeks after treatment, respectively.
ΔW(%): maximum reduction in body weight in animals in the first 3 weeks after receiving treatment.
RCO: mean relative cardiac output = ratio of the mean cardiac output measured in treated animals to the mean cardiac output measured in age-matched control.
RHR: mean relative heart rate = ratio of the mean heart rate measured in treated animals to the mean heart rate measured in age-matched control.
CHF: the total incidence of congestive heart failure over the course of study of 8 weeks. Symptoms of congestive heart failure are defined by the appearance of general subcutaneous oedema, ascites and/or pleural effusion.

I claim:

1. A method for the treatment of a patient in need of cardioprotection which comprises administering to said patient a therapeutically effective amount of a compound of formula (II):